United States Patent [19]

Tofe et al.

[11] 4,234,562

[45] Nov. 18, 1980

[54] RADIOGRAPHIC SCANNING

[75] Inventors: Andrew J. Tofe; Marion D. Francis, both of Cincinnati, Ohio

[73] Assignee: The Procter & Gamble Company, Cincinnati, Ohio

[21] Appl. No.: 888,599

[22] Filed: Mar. 20, 1978

Related U.S. Application Data

[63] Continuation of Ser. No. 701,478, Jun. 30, 1976, abandoned, which is a continuation of Ser. No. 462,477, Apr. 19, 1974, Pat. No. 3,983,227, which is a continuation-in-part of Ser. No. 363,286, May 23, 1973, abandoned.

[51] Int. Cl.$^2$ ............................................. A61K 29/00
[52] U.S. Cl. ........................................ 424/1; 252/408; 260/502.4 P; 424/9
[58] Field of Search .................... 252/408, 301.1 R; 424/1, 9, 198; 260/502.4 P, 429 R

[56] References Cited

U.S. PATENT DOCUMENTS 3,983,227   9/1976   Tofe et al. .............................. 424/1

*Primary Examiner*—Benjamin R. Padgett
*Assistant Examiner*—Christine M. Nucker
*Attorney, Agent, or Firm*—Jerry J. Yetter; Donald E. Hasse; Richard C. Witte

[57] ABSTRACT

A composition and method for the preparation of a technetium-99 m based scintigraphic scanning agent are disclosed. The agent is prepared by the addition of a pertechnetate-99 m solution to an anhydrous salt composition comprising a phosphonic acid or a pharmaceutically acceptable salt thereof and a non-toxic, water-soluble, anhydrous, stannous, ferrous or chromous salt of hydrochloric or sulfuric acid.

11 Claims, No Drawings

RADIOGRAPHIC SCANNING

RELATED APPLICATIONS

This is a continuation, of application Ser. No. 701,478 filed June 30, 1976, abandoned which is a continuation of application Ser. No. 462,477 filed Apr. 19, 1974, now U.S. Pat. No. 3,983,227, which is a continuation-in-part of application Ser. No. 363,286, filed May 23, 1973, now abandoned.

BACKGROUND OF THE INVENTION

This invention relates to scintigraphic scanning and more particularly to a composition and method for preparing a highly effective technetium-99m based bone-scanning agent.

For some time it has been recognized that conventional X-ray techniques are not entirely satisfactory for detecting many types of disorders at an early stage, thereby allowing effective treatment. An outstanding deficiency in X-ray examination is the inability of that technique to detect skeletal metastases in their incipient stages when meaningful treatment is possible.

Recent "bone-scanning" work for detecting metastases has been directed toward the use of radioactive isotopes, especially the isotope fluorine-18 ($^{18}F$) which selectively migrates to the skeleton and especially to "active" sites thereon such as the joints and tumor sites where it exchanges with the hydroxyl group in calcium hydroxyapatite. $^{18}F$, however, has certain limitations due to its short half-life (110 minutes); viz., a very short "shelf life" and high energy emission which makes it unsuited for use with certain detection equipment, notably the Anger scintillation camera. Additionally, it requires very expensive equipment to prepare and is therefore quite unsuited to preparation at the site of use.

The strontium 85 isotope ($^{85}Sr$) has also been used in bone scanning, seeking the skeleton to exchange with the calcium in calcium phosphate particularly at active sites. Strontium-85 is at the opposite end of the usable half-life spectrum from $^{18}F$, having a half-life of 65 days. While this greatly increased half-life (compared to $^{18}F$) provides a desirable "shelf-life", it requires that very long scan times be used to achieve a usable scan due to the low radiation emission rate.

Recently, and because of the shortcomings with the extremely short and long half-lives of $^{18}F$ and $^{85}Sr$, respectively, interest has been directed to technetium-99m ($^{99m}Tc$) which has a half-life of six hours. Interest in $^{99m}Tc$ has also increased due to the availability of convenient commercial means for generating it as needed. A $^{99m}Tc$ solution, in the oxidized pertechnetate ($^{99m}TcO_4^-$) form, is obtained from commercial generators by eluting them with an isotonic saline solution (0.9% by weight of sodium chloride). One commercial generator presently available to produce a pertechnetate solution is distributed by The E. R. Squibb Company and sold under the trademark Technetope$^R$ Hi-Con. Also, extracted $^{99m}TcO_4^-$ in isotonic saline is presently available from New England Nuclear of Boston, Massachusetts, under the designation Instant Tech.

Technetium-99m is different from either $^{18}F$ or $^{85}Sr$ in that it does not specifically seek or react with the skeleton. Its use therefore depends on compounding or complexing it with skeletal seeking materials. The first attempts at skeletal scanning with $^{99m}Tc$ utilized polyphosphates as the compounding/complexing agent and met with fair success.

Subsequent attempts to use $^{99m}Tc$ have involved mixing an aqueous solution of distannous-ethane-1-hydroxy-1,1-diphosphonate together with a solution of a non-stannous phosphonate. The resulting solution is then mixed with a pertechnetate to form a complex which seeks the skeleton. Such a system is reported by Yano et al. in *Journal of Nuclear Medicine,* Vol. 14, No. 2 at pp. 73–8, and Subramanian et al. in the *Journal of Nuclear Medicine,* Vol. 13, No. 12 at pp. 947–9. While this procedure has resulted in skeletal scans which are superior to those previously available, it too has shortcomings, most notably the limited stability of the distannous-ethane-1-hydroxy-1,1-diphosphonate solution.

The preparation of a soluble, stable dry system for use with a pertechnetate solution to form a bone scanning agent has met with difficulties. For instance, the use of a conventional technique, lyophilization (freeze drying) to form a suitable soluble, stable solid from an unstable solution has met with only limited success apparently because of hydrolytic problems with the stannous ion.

Accordingly, it is an object of this invention to provide a soluble, stable product which upon the addition of a pertechnetate solution forms an effective bone-scanning agent.

In addition, it is a continuing object of all work in the bone scanning area to provide a product which exhibits high skeletal selectivity (i.e., high ratio of uptake on the skeleton to uptake in the soft tissues).

SUMMARY OF THE INVENTION

These and other objects are provided by a composition comprising certain phosphonic acids or their pharmaceutically acceptable salts and a pharmaceutically acceptable stannous, chromous or ferrous salt.

In its method aspects, the present invention is a method of preparing a bone scanning agent comprising dissolving an anhydrous mixture of a phosphonate of enumerated classes and non-toxic water-soluble stannous, ferrous or chromus salt in a pertechnetate solution.

DETAILED DESCRIPTION OF THE INVENTION

This invention is based on the discovery that a stable $^{99m}Tc$ complex can be formed by the direct addition of a pertechnetate solution to a reducing metallic ion in a salt form in combination with certain mono-, di- and polyphosphonates, herein generally referred to as phosphonates, thereby allowing the simple production of a highly stable product which is suited for sale in kit form. The contents of a vial of the product, upon the addition of a pertechnetate solution, form a very effective bone-scanning agent.

THE PHOSPHONATES

A broad range of mono-, di- and polyphosphonic acids and their pharmaceutically acceptable salts are now known to concentrate on the skeleton upon injection of solutions thereof into a patient. Operable species for this purpose include mono-, di- and polyphosphonates selected from the group consisting of:

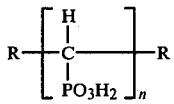

wherein each R is hydrogen or CH₂OH and n is an integer of from 3 to 10;

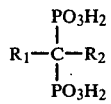

wherein $R_1$ is hydrogen, alkyl containing from 1 to about 20 carbon atoms, alkenyl containing from 2 to about 20 carbon atoms, aryl (e.g., phenyl, naphthyl), phenylethenyl, benzyl, halogen (e.g., chlorine, bromine and fluorine), hydroxyl, amino, substituted amino (e.g., dimethylamino, diethylamino, N-hydroxy-N-ethylamino, acetylamino), —CH₂COOH, —CH₂PO₃H₂, CH(PO₃H₂)(OH), or —[CH₂C(PO₃H₂)₂]ₙ—H where n=1 to 15, $R_2$ is hydrogen, lower alkyl (e.g., methyl, ethyl, propyl and butyl), amino, benzyl, halogen (e.g., chlorine, bromine, and fluorine), hydroxyl, —CH₂COOH, —CH₂PO₃H₂, or —CH₂CH₂PO₃H₂;

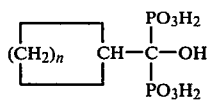

wherein n is an integer of from 3 to 9;

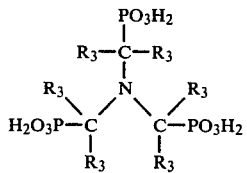

wherein each $R_3$ is hydrogen or lower alkyl (e.g., methyl, ethyl, propyl and butyl);

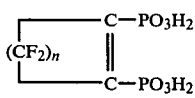

wherein n is an integer of from 2 to 4;

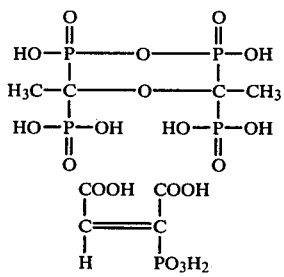

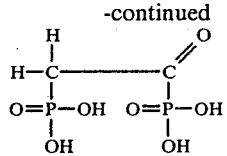

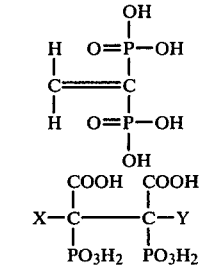

wherein X and Y are each hydrogen or hydroxy; and the non-toxic salts of each of the foregoing phosphonates which in an essentially neutral aqueous solution will react with hereinafter enumerated reducing/complexing materials; i.e., stannous, ferrous, or chromous salts to form the corresponding stannous, ferrous or chromous phosphonate salt. Suitable reactive phosphonate salts (hereinafter referred to as pharmaceutically acceptable salts) for use with the present invention include sodium, potassium, ammonium and low molecular weight substituted ammonium (e.g., mono-, di and triethanolamine and quaternary ammonium) salts of the above phosphonates and mixtures thereof.

Operable polyphosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid, nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, ammonium, triethanolammonium, diethanolammonium, and monoethanolammonium salts.

Propane-1,2,3-triphosphonic acid and salts thereof can be prepared by a process disclosed in the copending application of D. Allan Nicholson and Darrel Campbell, Ser. No. 82,819, filed Oct. 21, 1970, now U.S. Pat. No. 3,743,688.

Butane-1,2,3,4-tetraphosphonic acid and salts thereof can be prepared by a process disclosed in the copending application of D. Allan Nicholson and Darrel Campbell, Ser. No. 67,200, filed Aug. 26, 1970, now U.S. Pat. No. 3,755,504.

The higher aliphatic vicinal polyphosphonates and salts thereof can be prepared by the process disclosed in U.S. Pat. No. 3,584,035 granted June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphono-prop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-dihydroxyethyl)-aminomethanediphosphonic acid; N-acetylaminomethanediphosphonic acid; aminomethanediphosphonic acid; dihydroxymethanediphosphonic acid; and the pharmaceutically acceptable salts of these acids, e.g., sodium, potassium, ammonium, triethanolammonium, diethanolammonium, and monoethanolammonium salts.

Ethane-1-hydroxy-1,1-diphosphonic acid, an especially preferred polyphosphonate, has the molecular formula $CH_3C(OH)(PO_3H_2)_2$. (According to nomenclature by radicals, the acid might also be named 1-hydroxyethylidene diphosphonic acid.)

While any pharmaceutically acceptable salt of ethane-1-hydroxy-1,1-diphosphonic acid can be used in the practice of this invention, mixtures of the disodium and trisodium salts are most preferred. To other sodium, potassium, ammonium, and mono-, di-, and triethanolammonium salts and mixtures thereof are also suitable, provided caution is observed in regulating the total intake of cation species in the salt composition. These compounds can be prepared by any suitable method, however, an especially preferred method is disclosed in U.S. Pat. No. 3,400,149 granted Sept. 3, 1968.

Methanehydroxydiphosphonic acid and related compounds operable herein can be prepared, for example, by reaction of phosgene with an alkali metal dialkylphosphite. A complete description of these compounds and a method for preparing same is found in U.S. Pat. No. 3,422,137 granted Jan. 14, 1969.

Methanedihydroxydiphosphonic acid and salts useful herein and a method for preparing same are disclosed in U.S. Pat. No. 3,497,313 granted Feb. 24, 1970.

Methanediphosphonic acid and related compounds useful herein are described in detail in U.S. Pat. No. 3,213,030, granted Oct. 19, 1965. A preferred method of preparing such compounds is disclosed in U.S. Pat. No. 3,251,907 granted May 17, 1966.

Ethane-1,1,2-triphosphonic acid and related compounds which can be used in the compositions of this invention, as well as a method for their preparation, are fully described in U.S. Pat. No. 3,551,339 granted Dec. 29, 1970.

Propane-1,1,3,3-tetraphosphonic acid and related compounds useful herein, and a method for preparing same are fully disclosed in U.S. Pat. No. 3,400,176 granted Sept. 3, 1968. The higher methylene interrupted methylene diphosphonate polymers can be prepared by the polymerization of ethylene-1,1-diphosphonate.

Pentane-2,2-diphosphonic acid and related compounds can be prepared in accordance with the method described by G. M. Kosolopoff in *J. Amer. Chem. Soc.*, 75, 1500 (1953).

Operable phosphonates of formula (III) above include the following:
Methanecyclobutylhydroxydiphosphonic acid
Methanecyclopentylhydroxydiphosphonic acid
Methanecyclohexylhydroxydiphosphonic acid
Methanecycloheptylhydroxydiphosphonic acid
Methanecyclooctylhydroxydiphosphonic acid
Methanecyclononylhydroxydiphosphonic acid
Methanecyclodecylhydroxydiphosphonic acid Each of the sodium, potassium, ammonium, monoethanolammonium, diethanolammonium, and triethanolammonium salts of the above recited methanecycloalkylhydroxydiphosphonic acids as well as any other pharmaceutically acceptable salt of these acids, also selectively seek the skeleton.

The phosphonates of formula (III) can be prepared by methods fully described in U.S. Pat. No. 3,584,125, granted June 8, 1971.

The preferred phosphonates of formula (IV) for the purpose of this invention are tris(phosphonomethyl)amine; tris(1-phosphonoethyl)amine; tris(2-phosphono-2-propyl)amine; and their pharmaceutically acceptable salts. Tris(phosphonomethyl)amine is especially preferred. The following are exemplary of compounds which can also be used:
(a) bis(phosphonomethyl)-1-phosphonoethyl amine;
(b) bis(phosphonomethyl)-2-phosphono-2-propyl amine;
(c) bis(1-phosphonomethyl)phosphonomethyl amine;
(d) bis2-phosphono-2-propyl)phosphonomethyl amine;
(e) tris(1-phosphono-1-pentyl)amine;
(f) bis(phosphonomethyl)2-phosphono-2-hexyl amine; and
(g) the pharmaceutically acceptable salts of acids (a) through (f), e.g., sodium, potassium, ammonium, triethanolammonium, diethanolammonium, and monoethanolammonium salts.

The tris(phosphonoalkyl)amines can be prepared, for example, by first preparing the corresponding ester in accordance with the general reaction:

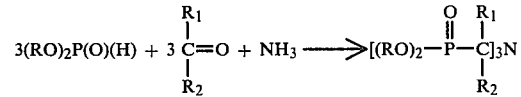

wherein R is alkyl and $R_1$ and $R_2$ are hydrogen or lower alkyl.

The free acids can be prepared by hydrolysis of the ester using strong mineral acids such as hydrochloric acid. The salts are, of course, prepared by neutralizing the acid with the base of the desired cation. The preparation of tris(phosphonoalkyl)amines is fully disclosed by Irani, et al., in Canadian Pat. No. 753,207, issued Feb. 21, 1967.

The phosphonates of formula (V) include the following; (1) 3,3,4,4,5,5-hexafluoro-1,2-diphosphonocyclopent-1-ene; (2) 3,3,4,4-tetrafluoro-1,2-diphosphonocyclobut-1-ene; and (3) 3,3,4,4,5,5,6,6-octafluoro-1,2-diphosphonocyclohex-1-ene.

The perfluorodiphosphonocycloalkenes can be prepared, for example, by reacting trialkyl phosphites with 1,2-dichloroperfluorocycloalk-1-enes in accordance with the procedures fully described by Frank in *J. Org. Chem.*, 31, #5, p. 1521.

The phosphonates of formula (VI) is referred to herein as cyclic tetraphosphonic acid. This compound and its pharmaceutically acceptable salts can be prepared by any suitable method, however, an especially preferred method is disclosed by Oscar T. Quimby, U.S. Pat. No. 3,387,024 granted June 4, 1968.

Operable phosphonates encompassed by the above formula (VII) are ethene-1,2-dicarboxy-1-phosphonic acid; and the pharmaceutically acceptable salts of these acids, e.g., sodium, potassium, ammonium, triethanolammonium, diethanolammonium, and monoethanolammonium salts. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Ethene-1,2-dicarboxy-1-phosphonic acid and related compounds useful herein can be prepared by reaction of an ester of acetylenedicarboxylic acid and a dialkyl phosphite followed by hydrolysis and saponification. This method is more fully described in U.S. Pat. No. 3,584,124, granted June 8, 1971.

The sodium salt of formula (VIII) can be made by the rearrangement reaction of a 2-haloethane-1-hydroxy-1,1-diphosphonic acid with about 3 equivalents of sodium hydroxide as disclosed in U.S. Pat. No. 3,641,126.

The phosphonate of formula (IX) can be made by the method of German Offenlegunsschrift No. 2,026,078.

Operable carboxyphosphonates of the above formula (X) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and the pharmaceutically acceptable salts of these acids, e.g., sodium, potassium, ammonium, triethanolammonium, diethanolammonium and monoethanolammonium salts.

Ethane-1,2-dicarboxy-1,2-diphosphonic acid, a preferred carboxyphosphonate herein, has the molecular formula $CH(COOH)(PO_3H_2)CH(COOH)(PO_3H_2)$. The most convenient crystallizable salts of this acid are obtained when three, four or five of the acid hydrogens are replaced by sodium.

While any pharmaceutically acceptable salt of ethane-1,2-dicarboxy-1,2-diphosphonic acid can be used in the practice of this invention, the tetrasodium dihydrogen salt, the trisodium trihydrogen salt, the disodium tetrahydrogen salt, the monosodium pentahydrogen salt, and the mixtures thereof are useful. The other potassium, ammonium, and mono-, di-, and triethanolammonium, etc., salts and mixtures thereof are also suitable, provided caution is observed in regulating the total intake of cation species in the salt composition.

Ethane-1,2-dicarboxy-1,2-diphosphonic acid and suitable salts thereof can be prepared in any convenient manner. For example, the reaction described by Pudovik in "Soviet Research on Organo-Phosphorus Compounds", 1949–1956, Part III, 547–85c. can be used to prepare the ester of ethane-1,2-dicarboxy-1,2-diphosphonic acid which in turn can, by ordinary hydrolysis reactions, be converted to the free acid form. Neutralization by alkali compounds such as sodium hydroxide, potassium hydroxide, carbonates and the like can be used to prepare a desired salt of the acid. A more detailed description of the preparation of these compounds is described in U.S. Pat. No. 3,562,166 granted Feb. 9, 1971.

Ethane-1,2-dicarboxy-1,2-dihydroxy-1,2-diphosphonic acid and related compounds useful herein can be prepared by reaction of an ester of ethane-1,2-dicarboxy-1,2-diphosphonic acid and an alkali metal hypohalite followed by hydrolysis and saponification. This method is more fully described in U.S. Pat. No. 3,579,570 granted May 18, 1971.

Mixtures of any of the foregoing phosphonic acids and/or salts can be used in the practice of this invention.

In a highly preferred embodiment of this invention, mixtures of disodium- and trisodium-ethane-1-hydroxy-1,1-diphosphonate salts wherein the mole ratio of the disodium salt to trisodium is from about 4:1 to 1:1, more preferably 3:1 to 1:1, are employed. These preferred phosphonate salt mixtures provide especially good scintiscans (excellent skeletal uptake and little soft tissue uptake).

For the reasons mentioned hereinafter, however, it is preferable to limit the amount of stannous, chromous or ferrous salts of the polyphosphonates to no more than about 5% of the total.

REDUCING/COMPLEXING MATERIALS

In order to reduce the pertechnetate solution, (for example, one from the aforementioned generator) and complex the resulting technetium-99m a stannous, chromous or ferrous salt is employed in the compositions of the present invention. The prior art has used an aqueous solution of distannousethane-1-hydroxy-1,1-diphosphonate as a reducing and complexing means. Such a solution, however, exhibits long-term instability (i.e., hydrolyzes and/or oxidizes) and therefore must be used in a relatively short time after its preparation. In partially successful attempts to solve this problem the prior art provided elaborate oxygen excluding packaging (e.g., glass ampules with the attendant possibility of glass fragments in the product) or, alternatively used large excesses of reducing metallic ions (e.g., stannous) to assure that, although some oxidation occurs, sufficient reducing capacity remains. The latter can result in introducing undesirably high levels of such metals into the patient. Another not fully satisfactory approach is to use highly acidic solutions in an attempt to minimize hydrolysis of the stannous ion.

It has now been found that certain stannous, chromous and ferrous salts (and especially the chloride and sulfate salts) together with the aforementioned phosphonates (and especially the preferred disodium- and trisodium-ethane-1-hydroxy-1,1-diphosphonate mixtures) are suitable in anhydrous form for addition of a pertechnetate solution to yield a bone scanning agent with excellent skeletal selectivity and low intake of metals. (For simplicity hereinafter, the term "agent" will be used to describe the product which is injected into the animal on which the skeletal scan is to be performed and the terms "kit" and "mix" will be used to refer to the ingredients for the agent but excluding the technetium solution which is subsequently added to form the agent.) Additionally, such dry form mix is virtually completely stable, thereby eliminating a major problem of the prior art. The efficacy of the agent prepared from the kits of the present invention is surprising in view of the difficulties encountered in attempts to prepare a suitable kit by lyophilizing the prior art solution, a conventional pharmaceutical technique for forming a stable dry product.

It has now been found that a highly effective and specific bone scanning agent is prepared upon the addition of a conventionally prepared pertechnetate solution to a mixture of a "reducing and complexing salt"

(i.e., an anhydrous non-toxic salt of the reducing and complexing stannous, ferrous and chromous ions) and a phosphonate of the above enumerated group. Espe- Examples of suitable kits made up according to this invention are glass vials containing the following (the quantities of each component being in mg.):

| Components | Kits | | | | | | | | | |
|---|---|---|---|---|---|---|---|---|---|---|
| | A | B | C | D | E | F | G | H | I | J |
| Disodium-ethane-1-hydroxy-1,1-diphosphonate | 6 | 6 | 6 | 6 | — | — | 6 | 3 | 4 | 3.5 |
| Trisodium-ethane-1-hydroxy-1,1-diphosphonate | — | — | — | — | — | — | — | — | 2 | 2.5 |
| Disodium-methane-diphosphonate | — | — | — | — | — | 4 | — | — | — | — |
| Trisodium-methane-diphosphonate | — | — | — | — | — | 2 | — | — | — | — |
| Dichloromethanediphosphonic acid | — | — | — | — | 6 | — | — | 3 | — | — |
| Stannous chloride | 0.16 | 0.16 | — | — | 0.16 | 0.16 | 0.08 | 0.08 | 0.16 | 0.16 |
| Ferrous sulfate | — | — | 0.16 | — | — | — | — | — | — | — |
| Chromous chloride | — | — | — | 0.16 | — | — | 0.08 | 0.08 | — | — |
| Sodium chloride | 27 | — | 27 | — | 27 | 27 | — | 27 | 27 | 27 |
| Glucose | — | 27 | — | 27 | — | — | — | — | — | — | cially preferred reducing and complexing salts are the chlorides and sulfates due to their widely acknowledged safety; the stannous salts thereof and particularly anhydrous stannous chloride being especially preferred (because of the ideal reduction potential of the stannous ion and absence of adsorbed water).

It has also been discovered that the proportions of the reducing and complexing salt to the phosphonate in the mix influence the efficacy of the resulting agent. For example, when employing a mix of stannous chloride and disodium ethane-1-hydroxy-1,1-diphosphonate, the resulting "active" complex in the agent is one involving technetium (reduced from the pertechnetate by the stannous ion) and distannousethane-1-hydroxy-1,1-diphosphonate. A scanning agent for a human of about 50–100 Kg requires only 10–15 milliCuries (mCi.) of $^{99m}Tc$ activity which corresponds to minute quantities of $^{99m}Tc$. The present invention uses substantially lower levels of reducing and complexing material (e.g. $Sn^{++}$) than the prior art. The preferred level, however, is substantially above stoichiometric and thereby provides some allowance for oxidation of the reducing agent prior to use. Only a very small percentage (e.g., 0.01%) of the stannous or other reducing ions initially present upon adding the mix to the pertechnetate solution is needed to reduce the pertechnetate to $^{99m}Tc$; the remainder forms stannous salts with the phosphonate being used. The stannous phosphonate thus formed is believed to form a complex with the $^{99m}Tc$. It appears, however, that formation and stabilization of the complex must be assured by substantial amounts of excess phosphonate or loss of $^{99m}Tc$-complex stability and hence loss of specificity for the bone is encountered. A preferred molar ratio of reducing ion (e.g., $Sn^{++}$) to phosphonate is about 1:15 to 1:80 with 1:30 to 1:60 being especially preferred.

Although not necessary to the practice of the present invention, it is preferable to use a pharmaceutically acceptable extender or filler to dilute the reducing and complexing salt in order to simplify metering the small quantities of such salt which are required. Sodium chloride and glucose are preferred; sodium chloride is especially preferred inasmuch as its addition will assure that the resulting agent is at least isotonic even if the pertechnetate solution is hypotonic as is the case when it must be diluted with sterile water to reduce its activity.

The above components are thoroughly mixed (e.g., in the compositions hereinafter described) and packaged under nitrogen blanketing in standard glass vials of about 5 ml capacity.

Each such kit upon the addition of about 5 ml pertechnetate-99m solution having about 50–75 mCi/ml activity and a thorough shaking yields an agent to be administered, e.g., by intravenous injection into a human. Preferably about 1 ml of solution is used in an adult of about 50–100 Kg body weight and is injected slowly; e.g., over a period of about 30 seconds. Lesser amounts can be used, if desired, in children and other small patients. Administration is preferably done within about three hours of preparation. Kits can, of course, contain multiples or fractions of the above amounts to allow preparation of sufficient agents from a single kit to perform any desired number of scans.

Agents prepared from mixture A have been used in humans with excellent results. In addition, various mixtures have been used in laboratory studies on rats which are a good human model in tests of the present invention. In rats, one-half the human dosages of the mixes have been used and 0.001 to 1 mCi of $^{99m}Tc$ have been used for distribution studies.

Distribution studies in man indicate that the agent produced from kit A with 15 mCi of activity at about three hours after injection, is typically distributed in a 70 Kg man as follows: 40–50% of the dose goes to the skeleton, 6% is in the blood and the remainder is excreted in the urine. This is a highly satisfactory distribution for safe and effective scans.

Optimum scanning time for bone scanning is about three hours post administration. If it were desired to detect calcific areas other than the bone, differing times would typically be used. For example, advanced calcific atherosclerosis and myocardial infarcts may be detected at varying times after injection, depending upon the regional blood clearance. Also, the phosphonates have some affinity for certain proliferative cells, e.g., those associated with stomach ulcers. Distribution of the above scanning agents to such sites will typically occur in about one hour; optimum scanning time, however, will obviously vary with the site to be scanned. Other variations within the scope of the following claims will occur to those skilled in the art.

What is claimed is:

1. A composition for the preparation of an improved bone scanning agent comprising a dry mixture of:
   (a) methanehydroxydiphosphonic acid and pharmaceutically-acceptable salts, and mixtures of salts, thereof; and
   (b) an amount of an anhydrous hydrochloric or sulfuric acid salt of a metal selected from the group consisting of ferrous, chromous and stannous and mixtures thereof sufficient to produce a molar ratio of metal to phosphonate of from about 1:15 to about 1:80.

2. A composition according to claim 1 wherein the phosphonate is a sodium salt or mixture of sodium salts.

3. A composition according to claim 2 wherein the phosphonate is a mixture of disodium and trisodium methanehydroxydiphosphonate salts.

4. A composition according to claim 1 wherein the metal ion is stannous.

5. A composition according to claim 4 wherein the metal salt is stannous chloride.

6. A composition according to claim 1 which additionally contains about 1 to 50 parts of sodium chloride.

7. A composition for the preparation of an improved bone scanning agent comprising a dry mixture of:

(a) a phosphonate selected from the group consisting of:

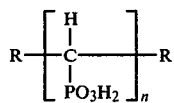

wherein each R is hydrogen or $CH_2OH$ and n is an integer of from 3 to 10;

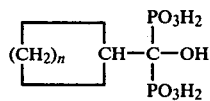

wherein n is an integer of from 3 to 9;

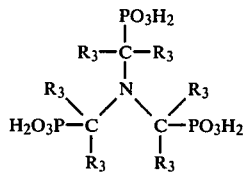

wherein each $R_3$ is hydrogen or lower alkyl;

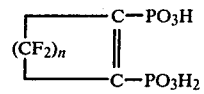

wherein n is an integer of from 2 to 4;

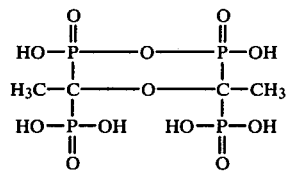

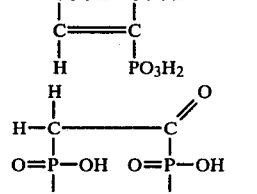

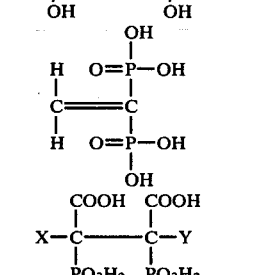

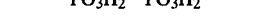

wherein X and Y are each hydrogen or hydroxy; and the pharmaceutically-acceptable salts of each of the foregoing acids and mixtures thereof; and (b) an amount of an anhydrous hydrochloric or sulfuric acid salt of a metal selected from the group consisting of ferrous, chromous and stannous and mixtures thereof sufficient to produce a molar ratio of metal to phosphonate of from about 1:15 to 1:80.

8. The composition of claim 7 wherein the metal ion is stannous.

9. The composition of claim 8 wherein the metal salt is stannous chloride.

10. The composition of claim 9 which additionally contains about 1 to 50 parts of sodium chloride.

11. A method for preparing an improved bone scanning agent comprising adding a pertechnetate solution to the dry mixture of claims 1 or 7.

* * * * *